United States Patent
Feldhues et al.

[11] Patent Number: 6,025,490
[45] Date of Patent: Feb. 15, 2000

[54] PROCESS FOR THE PREPARATION OF SUBSTITUTED 4,4'-DIAMINOSTILBENE-2,2'-DISULPHONIC ACIDS

[75] Inventors: Ulrich Feldhues, Charleston, S.C.; Rolf Brockmann, Bergisch Gladbach, Germany; Udo Eckstein, Köln, Germany; Detlef Szeymies, Kürten, Germany

[73] Assignee: Bayer Aktiengesellschaft, Leverkusen, Germany

[21] Appl. No.: 09/022,337

[22] Filed: Feb. 11, 1998

[30] Foreign Application Priority Data

Feb. 18, 1997 [DE] Germany ............................ 197 06 238

[51] Int. Cl.[7] .................................................. C07D 251/68

[52] U.S. Cl. .......................................... 544/193.2; 544/83

[58] Field of Search ................................ 544/197, 193.2, 544/83

[56] References Cited

U.S. PATENT DOCUMENTS

| | | | |
|---|---|---|---|
| 3,177,207 | 4/1965 | Siegel et al. ............................ | 260/240 |
| 3,655,574 | 4/1972 | Frischkorn et al. .................. | 252/301.2 |
| 3,895,009 | 7/1975 | Fringeli ................................. | 260/240.1 |
| 4,466,900 | 8/1984 | Horlacher et al. .................. | 252/301.23 |

FOREIGN PATENT DOCUMENTS

| | | |
|---|---|---|
| 0 626 374 A2 | 11/1994 | European Pat. Off. . |
| 195 00 791 C1 | 8/1996 | Germany . |
| 1 359 898 | 7/1974 | United Kingdom . |
| 2 203 426 | 10/1988 | United Kingdom . |
| WO 96/00220 | 1/1996 | WIPO . |

OTHER PUBLICATIONS

Abstract of WO 98/05653, Feb. 12, 1998, in English.

*Primary Examiner*—Richard L. Raymond
*Attorney, Agent, or Firm*—Joseph C. Gil; Richard E. L. Henderson

[57] ABSTRACT

A process for the preparation of compounds of the formula (I)

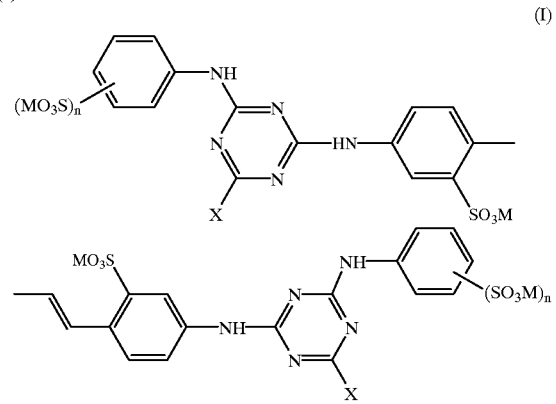

wherein
 n represents 0–2;
 M represents H, alkali metal ion or optionally substituted ammonium ion; and
 X represents anilino, N- or N,N-alkylamino;
by reaction of a compound of the formula (IV)

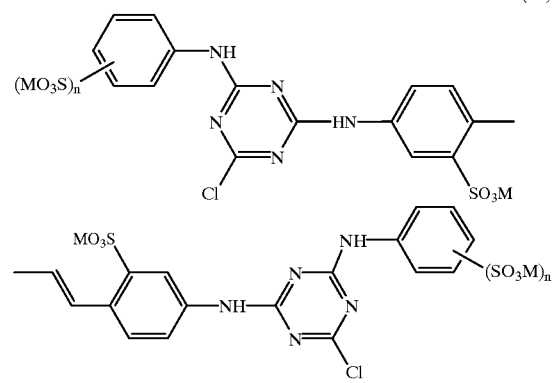

with 2 molar equivalents of an amnine of the formula X—H, at a pH of 5–10, optionally in the presence of an acid-trapping agent which differs from X—H, wherein the compound of the formula (IV) is added to an aqueous reaction medium with a temperature of at least 40° C. and the amine of the formula X—H and, optionally, the acid-trapping agent are added to the aqueous reaction medium independently of one another and/or during and/or after the addition of IV. The compounds of the formula I which are outstandingly suitable as optical brighteners.

10 Claims, No Drawings

PROCESS FOR THE PREPARATION OF SUBSTITUTED 4,4'-DIAMINOSTILBENE-2,2'-DISULPHONIC ACIDS

The invention relates to an improved process for the preparation of substituted 4,4'-diaminostilbene-2,2'-disulphonic acids and the use of products prepared in this way as optical brighteners.

It is already known from DE-A 19 500 791 to prepare specifically substituted 4,4'-diaminostilbene-2,2'-disulphonic acids by reaction of compounds of the formula

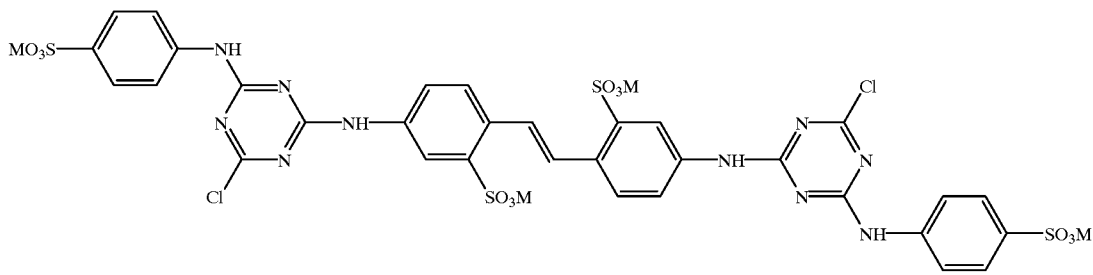

wherein

M represents an alkali metal ion or an optionally substituted ammonium ion, with 2 equivalents of a specific amine in the presence of an acid-trapping agent.

However, a disadvantage of the process variant described therein is that even before the desired reaction temperature is reached, thickening of the reaction mixture often occurs, which means that the stirrability is impaired. The stirrers used and their drive units are subjected to particularly heavy loads in this variant.

The object of the present invention was therefore to provide a process which no longer has the disadvantages mentioned.

A process has now been found for the preparation of compounds of the formula (I)

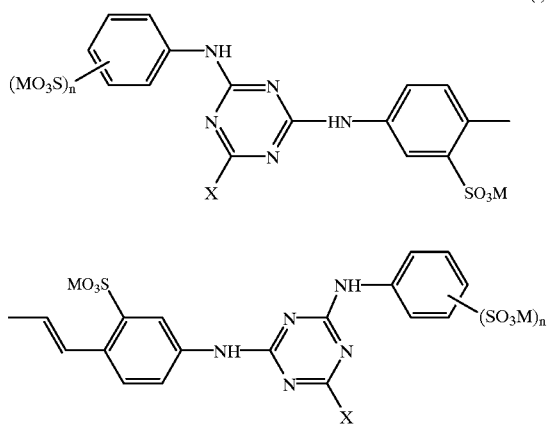

in which n represents 0, 1 or 2,

M represents hydrogen, an alkali metal ion or an optionally substituted ammonium ion and X represents anilino, N-alkylamino or N,N-dialkylamino, the optionally substituted alkyl radicals with N-alkylamino and N,N-dialkylamino optionally being interrupted by a hetero atom from the series consisting of O, N and S, and, in the case of N,N-dialkyl, the two alkyl radicals optionally forming, together with the N atom to which they are bonded, a saturated 5- or 6-membered heterocyclic ring, by reaction of a compound of the formula (IV)

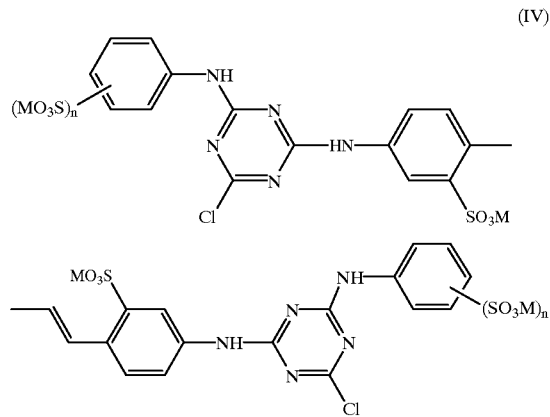

wherein M and n have the abovementioned meaning, with an amine of the formula (V)

$$X-H \quad (V)$$

wherein X has the abovementioned meaning, at a pH of 5–10, if appropriate in the presence of an acid-trapping agent which differs from V, characterized in that the compound of the formula (IV) is added to an aqueous reaction medium with a temperature of at least 40° C., and in that the amine of the formula (V) and, if appropriate, the acid-trapping agent are added to the aqueous reaction medium independently of one another before and/or during and/or after the addition of IV.

In a preferred embodiment of the process according to the invention,

M represents Na or K ions, $NH_4^+$ or triethanolammonium and n represents, in particular, zero.

The alkyl radicals in N-alkylamino and N,N-dialkylamino are preferably $C_1$–$C_4$-alkyl radicals, which are optionally interrupted by an O atom. Possible substituents of the alkyl radicals which may be mentioned are, for example, the substituents customary in the chemistry of whiteners, such as hydroxyl, cyano, carbamoyl or sulpho.

Examples of saturated 5- and 6-membered heterocyclic rings which can be formed from the two alkyl radicals of the N,N-dialkylamino group and the nitrogen atom to which they are bonded are, for example, pyrrolidine, piperidine, N-methylpiperazine, N-(2-hydroxyethyl)piperazine and, in particular, morpholine.

The aqueous reaction medium preferably has a temperature of at least 60° C., in particular 60 to 140° C., particularly preferably 80 to 100° C. The temperature of the reaction medium is preferably kept constant during the addition of IV to the reaction medium. For temperatures which lie above the boiling point of the reaction mixture, the reaction is preferably carried out under the autogenous pressure of the aqueous reaction medium up to 6 bar.

The temperature of the reaction medium is preferably 20° C., in particular 40° C. higher than that of the compound IV to be added.

The reaction of IV with V is preferably carried out at a pH of 6 to 9, in particular 7 to 8.

The amount of the amine V is preferably 2 or more molar equivalents, based on the compound of the formula (IV). If the process according to the invention is carried out without an acid-trapping agent which differs from V, it is preferably 4 to 5 molar equivalents.

Particularly preferably, the amine V is employed in an amount of 2 molar equivalents plus a 10–70% molar excess, together with an acid-trapping agent which differs from V.

Preferred amines of the general formula V are morpholine, methylamine, ethylamine, aniline, 2-hydroxyethylamine, 2-hydroxypropylamine and, in particular, di-(2-hydroxyethyl)amine and di-(2-hydroxypropyl)amine.

Suitable acid-trapping agents are water-soluble acid-binding agents, such as, for example, alkali metal hydroxides, such as NaOH or KOH, alkali metal carbonates, such as $Na_2CO_3$ or $K_2CO_3$, alkali metal bicarbonates, such as $NaHCO_3$ or $KHCO_3$, or tertiary amines, such as triethanolamine. These can be employed in solid form, for example by means of a conveying screw, or, preferably, in the form of their aqueous solutions.

Preferred acid-trapping agents are $Na_2CO_3$, $K_2CO_3$, NaOH or KOH, in particular in the form of their aqueous solutions.

The acid-trapping agent is preferably added separately. All or a portion of the acid-trapping agent can already be contained in the solution or suspension of IV, or all or a portion of it can be initially introduced into the aqueous reaction medium.

The addition of the acid-trapping agent is preferably pH-controlled. In particular, the acid-trapping agent is metered in automatically as a function of the pH.

In the case of pH-controlled addition of the acid-trapping agent, the pH chosen from the pH range from 5 to 10 serves as the control parameter. If the value falls below this set value, acid-trapping agent runs into the reaction mixture, which is preferably stirred, until the original value is reached again. This can be effected manually or, preferably, automatically with the aid of a titrator. A suitable titrator is, for example, a DULCOMETER® of the type PR F2K2 from Pro Minent®.

The deviation from the set pH in this process variant is as a rule not more than −0.5 or +0.3 pH units. When (IV) has been consumed and therefore no further hydrochloric acid is formed under these conditions, the pH chosen as the set value is established again without falling once more, and the flow stops.

In practice, the end point for the addition of the acid-trapping agent is already reached when less than 0.5% of the calculated amount of IV is consumed within 10 minutes.

The aqueous reaction medium is preferably water, which optionally already comprises a proportion or all of the amine V before the addition of the compound IV.

The compound of the formula (IV) can be added to the reaction medium in solid form or, preferably, as an aqueous solution or suspension.

If the compound of the formula (IV) is used as an aqueous solution or suspension, surfactants, such as, for example, alkoxylated fatty alcohols, can also be present.

In a preferred embodiment of the process according to the invention, the aqueous solution or suspension of IV already comprises all or a proportion of the amine V and preferably has a pH at which the amine V is present predominantly in the form of its protonated form of the formula VI

wherein
X has the abovementioned meaning. This pH depends on the pK value of the particular amine and is preferably 4 to 10, in particular 4–8.

The compound of the formula (IV) is particularly preferably employed in the form of an aqueous solution or suspension which comprises 1.8 to 2.7 molar equivalents of amine V in the predominantly protonated form VI. The pH at which more than 50% of the amine is present in protonated form depends of course on the pK value of the amine; the pH is preferably 4 to 10, in particular 4 to 8. For this case, if appropriate, up to 0.7 molar equivalent of the amine V, based on IV, are added to the aqueous reaction medium before, during or after the addition of the aqueous solution or suspension of IV.

A compound of the formula IV in the form of its synthesis solution or suspension is preferably used.

The preparation of IV is carried out here preferably either by reaction of a 4,4'-diaminostilbene-2,2'-disulphonic acid of the formula (II)

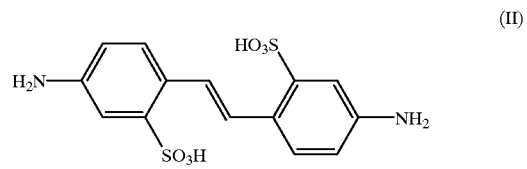

with 2 molar equivalents of cyanuric chloride, based on II, and subsequent reaction with 2 molar equivalents of an aniline of the formula (III)

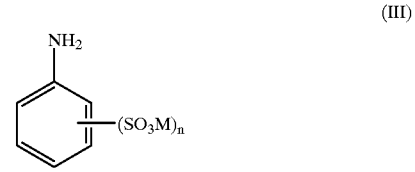

wherein
n and M have the abovementioned meaning, or by reaction of cyanuric chloride with 1 molar equivalent, based on the cyanuric chloride, of an aniline of the formula (III) and subsequent reaction with ½ molar equivalent of a compound of the formula (II).

The indication of the molar equivalents of the reactants employed for the preparation of the compound IV serves merely to indicate the stoichiometry, and does not exclude larger or smaller amounts, which may be more appropriate industrially.

In the preparation of the compound IV, for example, a dialkali metal salt of 4,4'-diaminostilbene-2,2'-disulphonic acid of the formula (II) in the form of an aqueous solution is added in a first stage to an aqueous cyanuric chloride suspension at a temperature of 0 to 25° C. and a pH of 3.5 to 5.5 in the presence or with simultaneous addition of an acid-binding agent, preferably an alkali metal carbonate, such as $Na_2CO_3$ or $K_2CO_3$, or an alkali metal bicarbonate, such as $NaHCO_3$ or $KHCO_3$, for neutralization of the hydrochloric acid liberated.

The aqueous cyanuric chloride suspension usually comprises 0.05–2% by weight (based on the cyanuric chloride) of a wetting surfactant, preferably from the series consisting of alkoxylated fatty alcohols, in particular one or more $C_8$–$C_{14}$-fatty alcohols with 3 to 10 mol of ethylene oxide and 0 to 25 mol of propylene oxide, for example the polyether from lauryl alcohol and 5 mol of ethylene oxide and/or the polyether of a $C_{10}$-alcohol and 6 mol of ethylene oxide and 8 mol of propylene oxide.

The cyanuric chloride suspension can furthermore also comprise 0.05 to 2.0% by weight (based on the cyanuric chloride) of a defoamer, of which, for example, about half consists of a mixture of $C_{15}$-alkanesulphamide and the ammonium salt of the $C_{15}$-alkanesulphonic acid and half consists of the corresponding $C_{15}$-alkane.

A preferred embodiment of the process according to the invention comprises carrying out the addition of the solution of (II), which additionally comprises an amount of a water-soluble acid-binding agent which is just sufficient to neutralize the hydrochloric acid formed during the reaction, to the aqueous cyanuric chloride suspension under pH control at a set pH from the range of 3.5–5.5, preferably 4.0 –5.0, at a temperature of 5 to 20° C., the deviation from the set value here also as a rule being not more than –0.5 or +0.3 pH units. In practice, the end point for the addition of the solution of (II) is also already reached here when less than 0.5% of the solution of (II) is consumed in 10 minutes.

In a second step, in this process variant, the compound (III) is allowed to run in and the temperature is preferably kept at 10–60° C., in particular at 20–40° C., and the pH is preferably kept at 3.5 to 7.5 by titration with an acid-trapping agent.

In a preferred embodiment for the preparation of the compound IV, the amine XH (V) is used as the acid-trapping agent in this second step.

Another preferred embodiment for the preparation of the compound IV comprises metering compounds of the general formula (III) into the aqueous cyanuric chloride suspension in a first step, during which the pH is kept constant (preferably at 1.5 to 6.0) by addition of acid-trapping agent. It is particularly advantageous if a solution or suspension of (III) additionally comprises an amount of a water-soluble acid-binding agent which is just sufficient to neutralize the hydrochloric acid formed during the reaction, and this solution or suspension of (III) is then metered into the aqueous cyanuric chloride suspension, if appropriate under pH control.

In a second reaction step, it is particularly advantageous to carry out the addition of a solution of (II), which additionally comprises an amount of a water-soluble acid-binding agent which is just sufficient to neutralize the hydrochloric acid formed during the reaction, to the aqueous reaction solution or suspension of the first step under pH control at a set pH of 3.5–7.0, preferably 4.5–6.0, at a temperature of 25 to 90° C., the deviation from the set value here also as a rule being not more than –0.5 or +0.3 pH units. In practice, the end point for the addition of the solution of (II) is also already reached here when less than 0.5% of the solution of (II) is consumed in 10 minutes.

The process according to the invention is particularly preferred for the preparation of the compounds of the formula (I) on an industrial scale, in particular for reaction volumes of 10 to 100 $m^3$.

Working up of the compounds of the general formula (I) prepared by the process according to the invention can be carried out in a known manner, for example by salting out and filtration, or (I) is precipitated out of the warm solution in a known manner, as free acid (M=H) which is sparingly soluble in water, and is filtered off.

For the preparation of a storage-stable liquid formulation, the moist crystal cake can then be dissolved in water in a known manner, if appropriate with addition of one or more formulating auxiliaries, such as nonionic or anionic surfactants and/or polar organic solubilizing agents, such as polyglycols or urea, and in the case of the free acid, a base is added in an amount such that this is converted back into a readily water-soluble salt. A simple, inexpensive working up which is likewise known comprises largely desalinating the crude solution of (I) by membrane separation processes under pressure (pressure permeation), concentrating it and converting it directly into the commercially available stable liquid formulation, for example in accordance with DE-C 32 34 784 or DE-A 22 04 725, or, if appropriate, drying it, in particular spray drying it.

This rational method of working up can be applied all the more successfully the purer the crude brightener solutions which the process provides, since the by-products and impurities, with the exception of the low molecular weight contents, are not sluiced with the permeate during the pressure permeation, and thus finally remain in the brightener preparation and may impair the efficiency thereof.

The process which has been improved according to the invention offers considerable advantages here over the processes known to date, since it provides the crude brightener solutions in a purity which has not hitherto been achieved without the additional purification steps, and with a considerably reduced waste water load for the user. By conventional working up by salting out or precipitation in the acid form, a much lower waste water load also results for the manufacturer than by the processes to date.

The compounds of the formula (I) prepared by the process according to the invention are important optical brighteners, inter alia for polyamide, cellulose, paper and detergents.

EXAMPLES

Example 1

700 ml of water and 10 g of sodium chloride were introduced into a reactor A and stirred for 10 minutes. 1.0 g of a polyether from isodecyl alcohol, 6 mol of ethylene oxide and 8 mol of propylene oxide was then added, while stirring, and the mixture was cooled to about 10° C.

100 g of cyanuric chloride (0.542 mol) were introduced, while stirring, rinsing was carried out with 100 ml of water and the suspension was stirred until the pH had fallen to 4.5.

An aqueous solution, which was cooled to 10° C. and comprised 0.3 mol of disodium 4,4'-diaminostilbene-2,2'-disulphonate and 0.3 mol of sodium carbonate in 1200 ml, was titrated in, the temperature of the reaction mixture being allowed to rise to 18° C. An automatic titrator which was set at the upper limit value of pH 4.5 was used for the addition.

Theoretically, 1084 ml could be consumed. The end point of the reaction was reached when less than 5 ml had been consumed within 10 minutes. This was the case after 2 to 2.5 hours at a consumption of 99% of theory. A readily stirrable pale yellow suspension was formed.

The titrator reservoir was changed. The titrator reservoir contained 87.2 g of 80% strength aqueous diethanolamine solution (0.664 mol). The contents of reactor A were subsequently stirred at pH 4.5 for a further 30 minutes. During this period, about 1 g of 80% strength aqueous diethanolamine solution was taken up.

500 ml of sodium sulphanilate solution, which comprised 0.528 mol of sodium sulphanilate in this 500 ml, were then allowed to run into reactor A in the course of 30 minutes, the temperature in reactor A being increased to 35° C. The mixture was subsequently stirred at 35° C. for 2 hours. Up to this point in time, about 74 g of 80% strength aqueous diethanolamine solution (0.56 mol) were metered in via the titrator. At the end of the after-stirring time, the uptake was less than 2 ml in 10 minutes.

The remainder of the aqueous diethanolamine solution was allowed to run in.

300 ml of water were initially introduced into a second reactor B and heated to 95° C.

The contents from reactor A were transferred to reactor B in the course of 1 hour. During this procedure, the temperature in reactor B was kept constant at 95° C. and the pH was kept constant at 7.5 by titration with a 15% strength sodium carbonate solution. The mixture was then heated at 100° C. for 1 hour, with continued titration.

3.4 kg of a crude aqueous solution having a specific extinction of 49 at 350 nm were obtained. The crude solution comprised 3.2% (0.11 kg) of sodium chloride and 9% (0.31 kg) of active substance, which corresponds to the compound of the formula

Example 3

700 ml of water and 10 g of sodium chloride were introduced into a reactor A and stirred for 10 minutes. 1.0 g of a polyether from isodecyl alcohol, 6 mol of ethylene oxide and 8 mol of propylene oxide were then added, while stirring, and the mixture was cooled to about 10° C.

100 g of cyanuric chloride (0.542 mol) were introduced, while stirring, rinsing was carried out with 100 ml of water and the suspension was stirred until the pH had fallen to 4.5.

An aqueous solution, which was cooled to 10° C. and comprised 0.3 mol of disodium 4,4'-diaminostilbene-2,2'-disulphonate and 0.3 mol of sodium carbonate in 1200 ml, was titrated in, the temperature of the reaction mixture being allowed to rise to 18° C. An automatic titrator which was set at the upper limit value of pH 4.5 was used for the addition.

Theoretically, 1084 ml could be consumed. The end point of the reaction was reached when less than 5 ml had been consumed within 10 minutes. This was the case after 2 to 2.5 hours at a consumption of 99% of theory. A readily stirrable pale yellow suspension was formed.

25 g of a 20% strength sodium chloride solution were added.

The titrator reservoir was changed. The titrator reservoir contained 87.2 g of an 80% strength aqueous diethanolamine solution (0.664 mol). The contents of reactor A were subsequently stirred at pH 5.5 for a further 30 minutes.

During this period, about 1 g of 80% strength aqueous diethanolamine solution was taken up.

50.2 g of aniline (0.54 mol) were then allowed to run in over a period of 30 minutes, the temperature in the reactor being allowed to rise to 25° C. The mixture was subsequently stirred at 25° C. for 1.5 hours. Up to this point in time, about 71 g of an 80% strength aqueous diethanolamine solution (0.54 mol) were metered in via the titrator. At the end of the after-stirring time, the uptake was less than 2 ml in 10 minutes.

300 ml of water were initially introduced into a second reactor B, the remainder of the diethanolamine solution (16.2 g) was added and the mixture was heated to 95° C.

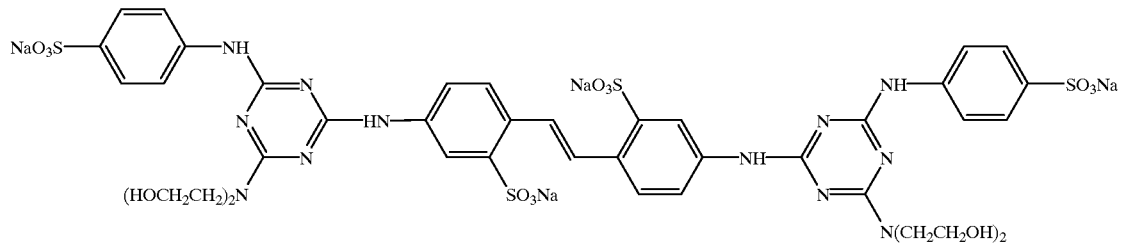

The crude solution was desalinated down to a residual content of 0.5% of sodium chloride by pressure permeation in the manner described in DE-C 32 34 784, Example 2, and then concentrated to a weight of 1.34 kg. A liquid formulation having a specific extinction of 125 at 350 nm, comprising 23% of active substance and having an electrolyte content of <0.5% was obtained.

Example 2

Example 1 was repeated, with the difference that 10% strength sodium hydroxide solution was employed as the acid-trapping agent in reactor B and the remainder of the aqueous diethanolamine solution was introduced into reactor B. Working up was carried out analogously to Example 1. 1.34 kg of a liquid formulation having a specific extinction of 125 at 350 nm were obtained.

The contents from reactor A were transferred to reactor B in the course of 1.5 hours. During this procedure, the temperature in reactor B was kept constant at 95° C. and the pH was kept constant at 7.5 by titration with 10% strength sodium hydroxide solution. The mixture was then heated at 98–100° C. for 2.5 hours with continued titration.

The mixture was allowed to cool to 85° C. and a pH of 4.2 was established at this temperature by addition of hydrochloric acid. The mixture was subsequently stirred for 30 minutes, during which it was allowed to cool to 50–55° C.

The product was filtered off and washed thoroughly with water. After drying at 50° C. in vacuo, 245 g of product were obtained.

The product corresponds to the compound of the formula

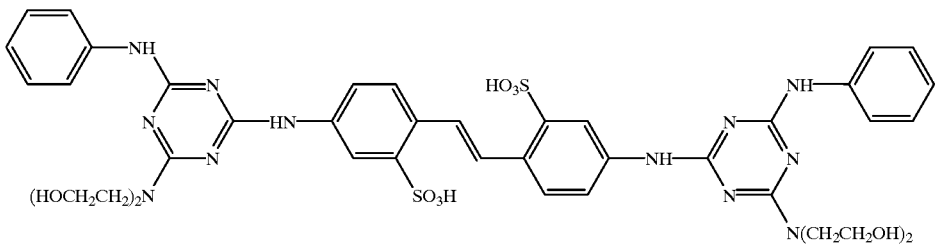

Example 4

700 ml of water and 10 g of sodium chloride were introduced into a reactor A and stirred for 10 minutes. 1.0 g of a polyether from isodecyl alcohol, 6 mol of ethylene oxide and 8 mol of propylene oxide were then added, while stirring and the mixture was cooled to about 10° C.

100 g of cyanuric chloride (0.542 mol) were introduced, while stirring, rinsing was carried out with 100 ml of water and the suspension was stirred until the pH had fallen to 4.5.

An aqueous solution, which was cooled to 10° C. and comprised 0.3 mol of disodium 4,4'-diaminostilbene-2,2'-disulphonate and 0.3 mol of sodium carbonate in 1200 ml, was titrated in, the temperature of the reaction mixture being allowed to rise to 18° C. An automatic titrator which was set at the upper limit value of pH 4.5 was used for the addition.

Theoretically, 1084 ml could be consumed. The end point of the reaction was reached when less than 5 ml had been consumed within 10 minutes. This was the case after 2 to 2.5 hours at a consumption of 99% of theory. A readily stirrable pale yellow suspension was formed.

100 g of a 20% strength sodium chloride solution were added.

The titrator reservoir was changed. The titrator reservoir contained 10% strength aqueous sodium hydroxide solution. The contents of reactor A were subsequently stirred at pH 6.5 for a further 30 minutes.

50.2 g of aniline (0.54 mol) were then allowed to run in over a period of 30 minutes, the temperature in the reactor being allowed to rise to 30° C. The mixture was subsequently stirred at 30° C. for 1 hour. For this, about 216 g of 10% strength aqueous sodium hydroxide solution (0.54 mol) were metered in via the titrator. At the end of the after-stirring time, the uptake was less than 2 ml in 10 minutes.

300 ml of water were initially introduced into a second reactor B, 56.6 g of morpholine (0.65 mol) was added and the mixture was heated to 95° C.

The contents from reactor A were transferred to reactor B in the course of 1 hour. During this procedure, the temperature in reactor B was kept constant at 95° C. and the pH was kept constant at 7.5 by titration with 10% strength sodium hydroxide solution. The mixture was then heated at 95–100° C. for 1 hour at pH 8.5 with continued titration. Thereafter, the mixture was heated at 135° C. for 1 hour.

The mixture was allowed to cool to 90° C. and 100 g of sodium hydroxide solution, 50% strength, were added. The mixture was filtered over a suction filter and the solid was washed thoroughly with hot dilute sodium chloride solution.

After drying at 100° C. in vacuo, 260 g of product were obtained.

The product corresponds to the compound of the formula

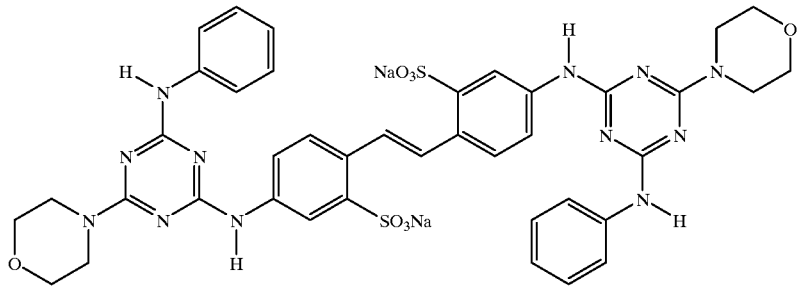

Example 5

700 ml of water and 10 g of sodium chloride were introduced into a reactor A and stirred for 10 minutes. 1.0 g of a polyether from isodecyl alcohol, 6 mol of ethylene oxide and 8 mol of propylene oxide was then added, while stirring, and the mixture was cooled to about 10° C.

100 g of cyanuric chloride (0.542 mol) were introduced, while stirring, rinsing was carried out with 100 ml of water and the suspension was stirred until the pH had fallen to 4.5.

An aqueous solution, which was cooled to 10° C. and comprised 0.3 mol of disodium 4,4'-diaminostilbene-2,2'-disulphonate and 0.3 mol of sodium carbonate in 1200 ml, was titrated in, the temperature of the reaction mixture being allowed to rise to 18° C. An automatic titrator which was set at the upper limit value of pH 4.5 was used for the addition.

Theoretically, 1084 ml could be consumed. The end point of the reaction was reached when less than 5 ml had been consumed within 10 minutes. This was the case after 2 to 2.5 hours at a consumption of 99% of theory. A readily stirrable pale yellow suspension was formed.

100 g of a 20% strength sodium chloride solution were added.

The titrator reservoir was changed. The titrator reservoir contained 10% strength aqueous sodium hydroxide solution. The contents of reactor A were subsequently stirred at pH 6.5 for a further 30 minutes.

50.2 g of aniline (0.54 mol) were then allowed to run in over a period of 30 minutes, the temperature in the reactor being allowed to rise to 30° C. The mixture was subsequently stirred at 30° C. for 1 hour. For this, about 216 g of 10% strength aqueous sodium hydroxide solution (0.54 mol) were metered in via the titrator. At the end of the after-stirring time, the uptake was less than 2 ml in 10 minutes.

67.2 g of methylamine solution, 30% strength (0.65 mol) were added.

300 ml of water were initially introduced into a second reactor B and the mixture was heated to 95° C.

The contents from reactor A were transferred to reactor B in the course of 1 hour. During this procedure, the temperature in reactor B was kept constant at 95° C. and the pH was kept constant at 7.5 by titration with 15% strength sodium carbonate solution. The mixture was then heated at 95–100° C. for 1 hour at pH 8.5 with continued titration. Thereafter, 100 g of sodium hydroxide solution, 50% strength, were added. The excess methylamine was allowed to escape by passing in nitrogen.

After the spray drying, 215 g of product were obtained.

The product corresponds to the compound of the formula

Example 6

A reactor A contained a solution of 167 g of 4,4'-bis[(4-(2,5-disulpho)anilino-6-chloro-1,3,5-triazin-2-yl)amino]-stilbene-2,2'-disulphonic acid hexasodium salt in 1275 ml of water.

200 ml of water and 44 g (0.335 mol) of diethanolamine solution (80% strength) were initially introduced into a second reactor B and were heated to 95° C.

The contents from reactor A were transferred to reactor B in the course of 1 hour. During this procedure, the temperature in reactor B was kept at 95° C. and the pH was kept at 7.5 by titration with 15% strength sodium carbonate solution. The mixture was then heated at 98–100° C. for 1.5 hours at pH 7.5, with continued titration.

The crude solution was desalinated down to a residual content of 0.5% of sodium chloride by pressure permeation in the manner described in DE-C 32 34 784, Example 2 and then concentrated to a weight of 0.8 kg. A liquid formulation having a specific extinction of 100 at 350 nm, comprising 22% of active substance and having an electrolyte content of <0.5% was obtained.

The active substance corresponds to the compound

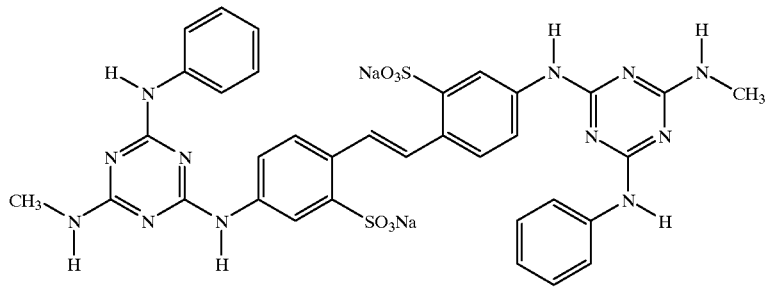

45

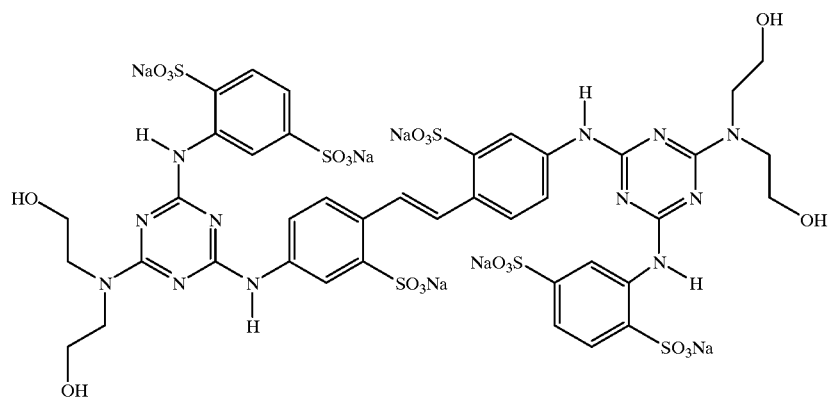

What is claimed is:

1. A process for the preparation of a compound of the formula (I)

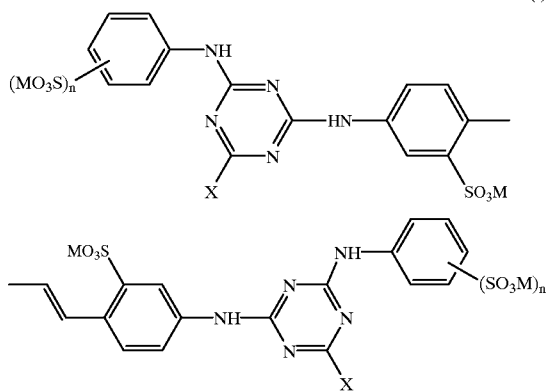

in which n represents 0, 1, or 2,

M represents hydrogen, an alkali metal ion, or an unsubstituted or substituted ammonium ion, and X represents (i) anilino, (ii) N-alkylamino wherein the alkyl groups are optionally substituted and/or optionally interrupted by a heteroatom selected from the group consisting of O, N, and S, or (iii) N,N-dialkylamino wherein the alkyl groups independently are optionally substituted and/or optionally interrupted by a heteroatom selected from the group consisting of O, N, and S or the alkyl groups together with the nitrogen atom to which they are bonded form a saturated 5- or 6-membered heterocyclic ring, comprising reacting in an aqueous reaction medium having a temperature of at least 40° C. and a pH of 5 to 10

(1) a compound of the formula (IV)

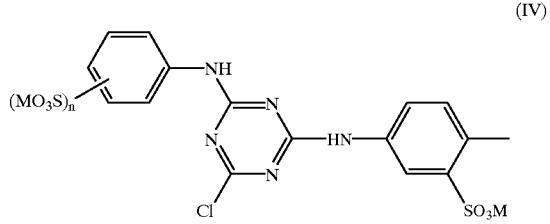

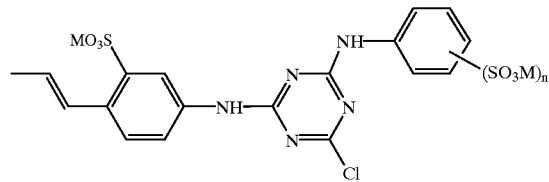

wherein M and n have the same meaning as above, with (2) an amine of the formula (V)

$$X-H \quad (V)$$

wherein X has the same meaning as above, and (3) optionally, an acid-trapping agent other than an amine of formula (V), wherein the temperature of the aqueous reaction medium is at least 20° C. higher than the temperature of the compound of formula (IV) being added and wherein the amine of formula (V) and the optional acid-trapping agent are independently added to the aqueous reaction medium before and/or during and/or after the addition of the compound of formula (IV).

2. The process according to claim 1 wherein the aqueous reaction medium has a temperature of 60 to 140° C.

3. The process according to claim 1 wherein the aqueous reaction medium has a temperature of 80 to 100° C.

4. The process according to claim 1 wherein the reaction is carried out data pH of 6 to 9.

5. The process according to claim 1 wherein the reaction is carried out at a pH of 7 to 8.

6. The process according to claim 1 wherein the compound of the formula (IV) is employed as an aqueous solution or suspension.

7. The process according to claim 1 wherein the aqueous solution or suspension of the compound of the formula (IV) already contains all or a portion of the amine of the formula (V).

8. The process according to claim 1 wherein the acid-trapping agent is an alkali metal hydroxide, alkali metal carbonate, alkali metal bicarbonate, or tertiary amine.

9. The process according to claim 1 wherein the acid-trapping agent is metered in automatically as a function of the pH.

10. The process according to claim 1 wherein n represents 0.

* * * * *